United States Patent [19]

Edwardson

[11] Patent Number: 5,064,372
[45] Date of Patent: Nov. 12, 1991

[54] ARTICULATOR FOR USE IN MAKING DENTURES OR PARTS THEREOF

[75] Inventor: Svante R. Edwardson, Solna, Sweden

[73] Assignee: Dentatus International AB, Hagersten, Sweden

[21] Appl. No.: 343,609

[22] Filed: Apr. 27, 1989

[51] Int. Cl.$^5$ .............................................. A61C 11/00
[52] U.S. Cl. ....................................... 433/66; 433/60; 433/64
[58] Field of Search ....................... 433/54, 57, 61, 62, 433/63, 64, 65, 66, 60

[56] References Cited

U.S. PATENT DOCUMENTS

| | | | |
|---|---|---|---|
| 2,608,762 | 9/1952 | Fox | 433/64 |
| 2,621,407 | 12/1952 | Schlesinger | 433/64 |
| 3,019,529 | 2/1962 | Hinze | 433/62 |
| 3,815,242 | 6/1974 | Martfay et al. | 433/63 |
| 4,163,319 | 8/1979 | Ouaknine | 433/64 |
| 4,200,981 | 5/1980 | Fine | 433/60 |
| 4,358,269 | 11/1982 | Hay et al. | 433/60 |
| 4,371,338 | 2/1983 | Mercer et al. | 433/60 |
| 4,391,589 | 7/1983 | Monfredo et al. | 433/63 |
| 4,624,639 | 11/1986 | Wong | 433/63 |
| 4,744,751 | 5/1988 | Finkelstein et al. | 433/65 |

FOREIGN PATENT DOCUMENTS 2549715 2/1985 France .................................. 433/63

OTHER PUBLICATIONS

Two page Dentatus pamphlet.

Primary Examiner—Gene Mancene
Assistant Examiner—Michael Lynch
Attorney, Agent, or Firm—Young & Thompson

[57] ABSTRACT

An articulator, for use in making dentures or parts thereof. It has an upper principal member and a lower principal member. An upper support is provided for holding a maxillary cast fixedly mounted on the side of the upper member facing the lower principal member. A lower support holds a mandibular cast. This support is mounted on the lower principal member and faces the upper principal member. The lower support has a releasing/locking arrangement making it possible for an operator to move the lower support freely in several directions when the arrangement is in its released mode and to lock it in a desired position requiring only a slight holding in place of the casts in relation to each other by the operator during a locking procedure.

8 Claims, 7 Drawing Sheets

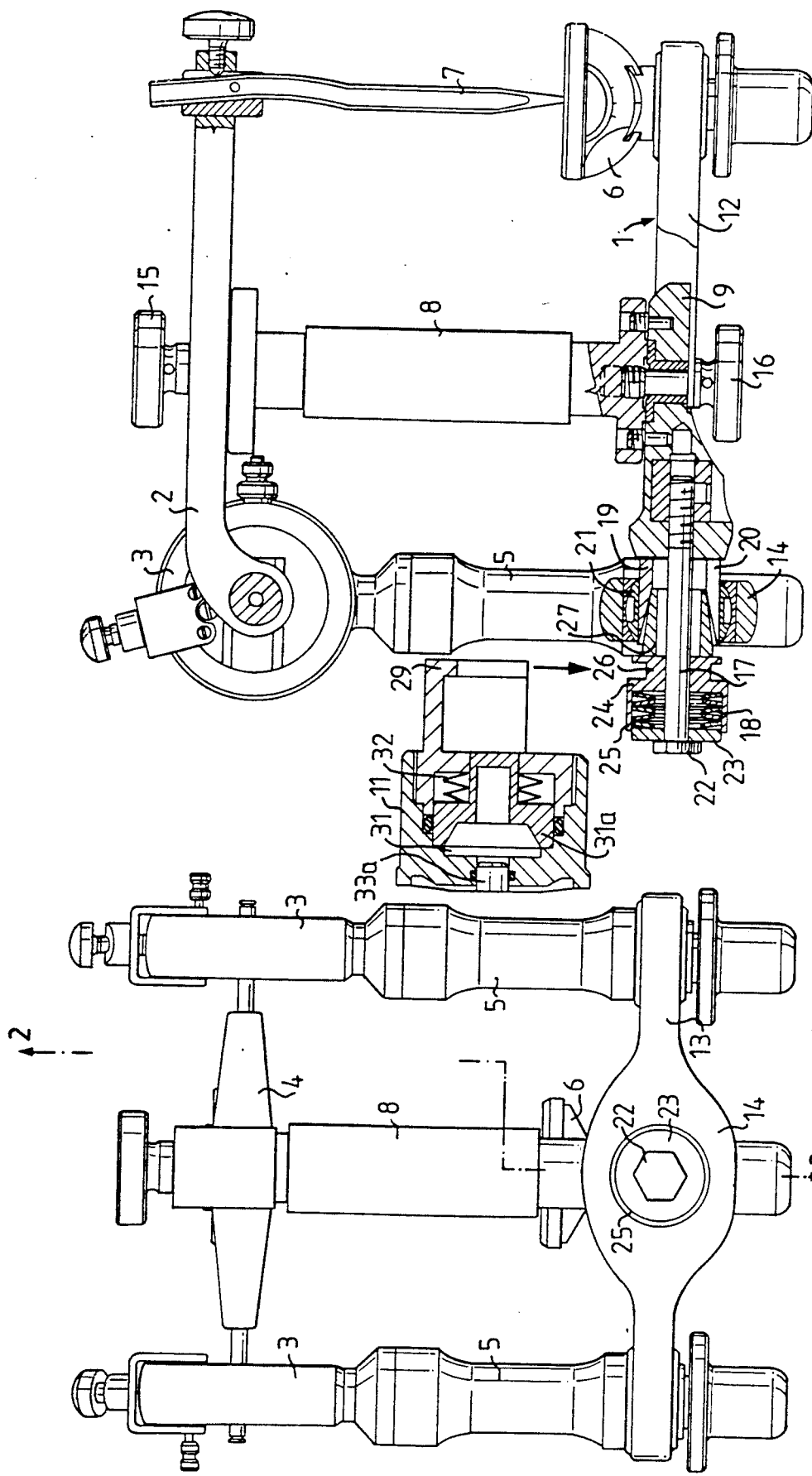

ARTICULATOR FOR USE IN MAKING DENTURES OR PARTS THEREOF

The present invention relates to an articulator, for use in making dentures or parts thereof, comprising a lower and an upper principal member which are interconnected by means of a condular mechanism that allows relative movement between said principal members, and which lower principal member is substantially horizontal and has an incisal table at its end away from said condular mechanism, and the upper principal member is set substantially horizontal by setting an incisal pin suspended from the upper principal member and supported at its lower end by said incisal table at its zero position or can be set at a small angle to a horizontal line. A maxillary cast is intended to be attached to the upper principal member and a mandibular cast is intended to be attached to the lower principal member.

Numerous types of articulators for simulating a patient's bite and jaw movements are found on the market. Many of them allow various kinds of adjustment from individual records in order to facilitate an accurate reproduction of the individual jaw movements.

In working with an articulator the upper, maxillary cast of a patient's jaw is first fixed in the upper part of the articulator either by plastering or by mechanical fixation. The plastering may be provided either by facebow registration using a bite-fork, the result of which being transferred to the articulator in connection with the plastering operation, or by means of mounting tables adapted to the articulator. Then, the lower, mandibular cast is adapted to the maxillary cast by means of a jaw impression in wax (wax index) by plastering or by mechanical fixation.

It happens sometimes that the dental technician working with the cast in the articulator discovers that the wax index taken by the dentist must be wrong, after the operation mentioned above is finished.

The technician then asks the dentist to take a new index of the patient's jaws. If the mandibular cast is already plastered the technician must make a new plaster cast with the new index.

There is an articulator on the market, type ARO sold by Dentatus International AB, in which a part of the lower member of the articulator onto which the mandibular cast is plastered is loosenable or releasable by means of a lever in such a way that it is movable in all possible directions. After a new wax index has been provided the released part of the lower member bearing the mandibular cast can be locked again in a new position relative to the maxillary cast. Therefore, there is no need to discard the original plaster cast in this type of articulator.

This prior art articulator was put on the market about 20 years ago. Even though the experts think this prior art articulator is good it has not been a success on the market. The reason for this is mainly that the people working with it (technicians or students or universities) have some difficulty in locking the part of the lower member in the right position after the new index has been inserted. This follows from the fact that it takes a lot of force to turn the lever during the locking operation and because while applying the same force it is difficult to hold the part of the lower member with the mandibular cast together with the new wax index in place relative to the maxillary cast on the upper member.

The main object of the invention is therefore to provide a releasable and lockable arrangement in which the operator of the articulator does not have to apply two mutually counteracting forces manually.

A further object of the invention is to provide a releasable and lockable arrangement in which the operator does not need to use any manual force at all.

The invention will now be described with reference to the accompanying drawings, wherein:

FIG. 1 is an elevational view of an articulator according to the invention,

FIG. 2 is a sectional view along the line 2—2 in FIG. 1 and has also some other parts cut away and shows the releasable/lockable part of the lower member in a locked position, FIG. 3 shows the same sectional view as FIG. 2 but shows the releasable/lockable part of the lower member in a released position and having the casts together with the wax index mounted in place, FIGS. 4A to 4H are schematic perspective views showing different operational steps in working with the articulator shown in FIGS. 1 to 3, FIGS. 5 to 7 are schematic sectional views of a second embodiment of the articulator according to the invention in different working positions, FIG. 8 is a sectional view along the line 8—8 in FIG. 7, FIG. 9 is a view from above of the mandibular cast holding means having a part of its central part cut away, and FIG. 10 is a half sectional view of the device shown in FIG. 9 cut along the line 10—10 in FIG. 9.

As can be seen from FIGS. 1 to 3, an articulator comprises a lower principal member 1 and an upper principal member 2. The principal members 1 and 2 are at their rear end interconnected by a condylar mechanism including two condylar means 3 that allow relative movement between said principal members 1 and 2 simulating the movements of the jaw joint in a human being. The condylar means 3 are not a part of the invention and are therefore not described in detail. The condylar means 3 are connected to each other by means of an axle 4 running through the center of them. The lower member 1 is provided with support means 5 for the condylar means 3.

An incisal table 6 is located in the front end of the lower principal member 1. An incisal pin 7 of a type common in the art is settably disposed in the front end of the upper part and set to rest on the incisal table 6 with its lower end. The scale of the incisal pin 7 is set on a zero position and the pin is locked in this position. A gauge block 8 is provided between the upper and lower members 1 and 2, respectively. The lower member 1 includes a movable releasable/lockable part 9 on which the gauge block 8 is mounted for this setting operation. The part 9 is in a released mode during the setting and the setting of the pin 7 at zero position serves to place the part 9 in a central starting position. The releasing is affected by means of a hydraulic/pneumatic device 11 in a way which will be described later instead of a combined hydraulic/pneumatic device 11 as shown in FIGS. 2, 3 and 4 a purely hydraulic or pneumatic device or even an electrically driven device could be used. The main feature of this embodiment is that an auxiliary device driven by an external power source is used to help the operator in his work.

The lower member 1 is composed of a ring fixedly mounted to the support means 5 which ring in turn is composed of a front U-formed part 12 and a rear straight part 13 between the support means 5 having a wide portion 14 in the middle. The lower member has the movable part 9 placed within the ring and adapted to bear the mandibular cast 35 plastered to it on a mounting plate 35a. The part 9 is releasably/lockably attached to the wide portion 14 of the rear part 13.

As is common in the art the gauge block is fastened to the upper and lower members of the articulator by means of screws 15 and 16, respectively, used to fasten respective mounting plates 34a and 35a for the plastering in a way common in the art and therefore not described. The mounting plate 35a for the plastering of the mandibular cast 35 is provided on the movable part 9.

According to the invention the attachment of the movable part 9 is lockable in such a way that the operator can hold the maxillary and the mandibular casts 34 and 35 together on each side of the wax index 345 without any need to counteract any force exerted on the casts. In FIGS. 1 to 3 the part 9 has an axle 17 extending through an opening in the wide part 14. In the embodiment shown in FIGS. 1 to 3 no force at all is needed from the operator for the locking operation. The operator can thus concentrate on holding the casts together in position around the wax index while using very little manual force in doing so. The force is provided by the hydraulic/pneumatic device 11 which is operated by the operator by operating a knob or a foot pedal or the like (see FIG. 4H).

The construction could of course be such that a hydraulic pressure is inherent in piston in the lower member 1, when the part 9 is locked to the member 14, which pressure is released when the part 9 is to be released.

However, in FIGS. 1 to 3 the locking is effected by a strong spring 18, preferably a plate spring, which is slacked by means of a hydraulic/pneumatic means 11. The last mentioned alternative is to be preferred because there is no risk then that the hydraulic power will be lost during work as could be the case in the first mentioned alternative.

As shown best in FIGS. 2 and 3 the releasing/locking arrangement of the articulator has a front portion attached to the rear end of the mandibular cast holding part 9 comprising a ring 19 extending rearwardly around the axle 17 but at some radial distance therefrom and having elongated, axially extending slots 20. The rear part of the ring is tapered on its inner side and has an outwardly extending flange at its end serving as a stop against the rear side of the wider portion 14.

A bushing arrangement 21 of a type known per se and adapted to permit angular, turning and axial movements of the rear end of the part 9 is provided in the wider portion 14. The rear end of the axle 17 has a bolt head 22, a circular plate 23 abutting the bolt head, the cup spring 18 abutting the plate and a ring shaped locking device 24.

The device 24 has on its rear side a shielding cup-shaped portion 25 extending around the spring 18 and having an inner diameter adapted to let the shielding portion 25 run axially around the plate 23, a middle portion 26 having an inner diameter slightly larger than the diameter of the axle 17 such that the locking device can run easily along the axle 17, and at its front end a ringshaped locking means 27 having a tapered outer form adapted to the inner form of the ring 19 such that it will press the slotted ring 19 outwardly against the bushing 21 when pressed into contact with it by the action of the strong spring 18.

The bushing 21 is such that the mandibular cast holding part 9 is movable both in axial direction through it and in any possible angular direction because the bushing 21 has a movable part formed as a ring having an outer spherical periphery. The bushing 19 has also a slot (not shown) such that it can be pressed against the inner wall of the wider part 14 when the locking means 27 presses the slotted ring 19 outwardly. Thus the spring force of the spring 18 locks the part 9 both axially and angularly.

FIG. 2 shows the releasable/lockable arrangement in its locked condition and the hydraulic/pneumatic device 11 not connected to the arrangement. FIG. 3 shows the same arrangement in its released condition in which the hydraulic/pneumatic device 11 is connected to the arrangement and compresses the spring 18 by drawing the locking device 27 outwardly with a claw hook 29 in an annular groove 30 in the outer part of the middle portion 26 of the rear part 22 to 27 of the locking arrangement of the part 9 while abutting the end of the bolt head 22. This is affected by having the claw hook means 29 fixedly mounted in the device 11 and by pressing an inner, front plunger 31a against the action of a spring 32, preferably a cup spring, towards the bolt head 22. The hydraulic/pneumatic device 11 has a first, rear chamber 33 into which a pneumatic medium (air) is forced when the operator is operating a foot pedal (only shown in FIG. 4H) or the like. The pneumatic medium forces a rear plunger 33a to move to the right to take the position shown in FIG. 3, in which position a narrow part of the rear plunger 33a enters a second, front chamber 31 filled with a hydraulic medium, such as oil. The intrusion of the front end of the rear plunger 33a forces the front plunger 31a forward against the force of the spring 32. Hydraulic medium can be refilled through the nipple means 38 (FIG. 3). The operating pneumatic pressure may for instance be chosen to be an overpressure of 3 to 7 bars and the device is dimensioned such that this will for instance give the hydraulic side an overpressure of between 60 and 140 bars, which for instance will give an output power between 450 and 1050 kp.

FIG. 3 also shows the maxillary and mandibular casts 34 and 35, respectively, plastered to the upper part 2 and the movable part 9, respectively.

The operation of the device according to the embodiment shown in FIGS. 1 to 3 will now be described with reference to FIGS. 4A to 4H which shows the principles according to the invention tested on a test installation made to prove the invention, schematic views being drawn of the installation in different positions:

FIG. 4A shows the setting to a central position of the articulator by using the gauge block 8. The central position setting is performed because the lower member 1 including the part 9 should be able to be adjusted in the same manner in each direction from a central position when the part 9 is loosened. In FIG. 4A the articulator is turned upside down, and is placed on a separate support 36, which supports the upper part 2 of the articulator (now turned downwards) and the axle 4 at two points near each of the condylar means 3. The hydraulic/pneumatic means 11 has released the part 9 of the lower part 1 such that it is free to be adapted to the gauge block. The incisal pin 7 is placed to rest with its tip at the incisal table 6 and is locked in a position having its scale on zero position. Thereafter the hydraulic/pneumatic means 11 is operated to lock the part 9 and is then removed from the articulator. After that the gauge block 8 is taken away. The part 9 of the lower member 1 is now locked in a central position.

FIG. 4B shows the articulator turned to its right side having it lower member 1 with the part 9 which now is locked turned downwards. The plastering of the upper, maxillary cast 34 is finished.

FIG. 4C shows once again the articulator turned upside down having its lower member 1 turned upwards and placed on the support 36. The upper, maxillary cast is plastered to the upper member 2 of the articulator and the mandibular cast has been plastered to the movable, releasable/lockable part 9 of the lower member 1. At this point the operator then finds that the wax index was erronously taken. Because of this the mandibular cast 35 must be released in order to use a new wax index.

FIG. 4D shows how the part 9 of the lower member 1 is loosened by aid of the hydraulic/pneumatic device 11.

FIG. 4E shows (the articulator being turned upside down) how the upper and lower casts 34, 35 are adapted to each other by means of a new wax index. The movable part 9 of the articulator is held freely movable by means of the hydraulic/pneumatic device 11 set in the operating mode shown in FIG. 3.

Figure 3:
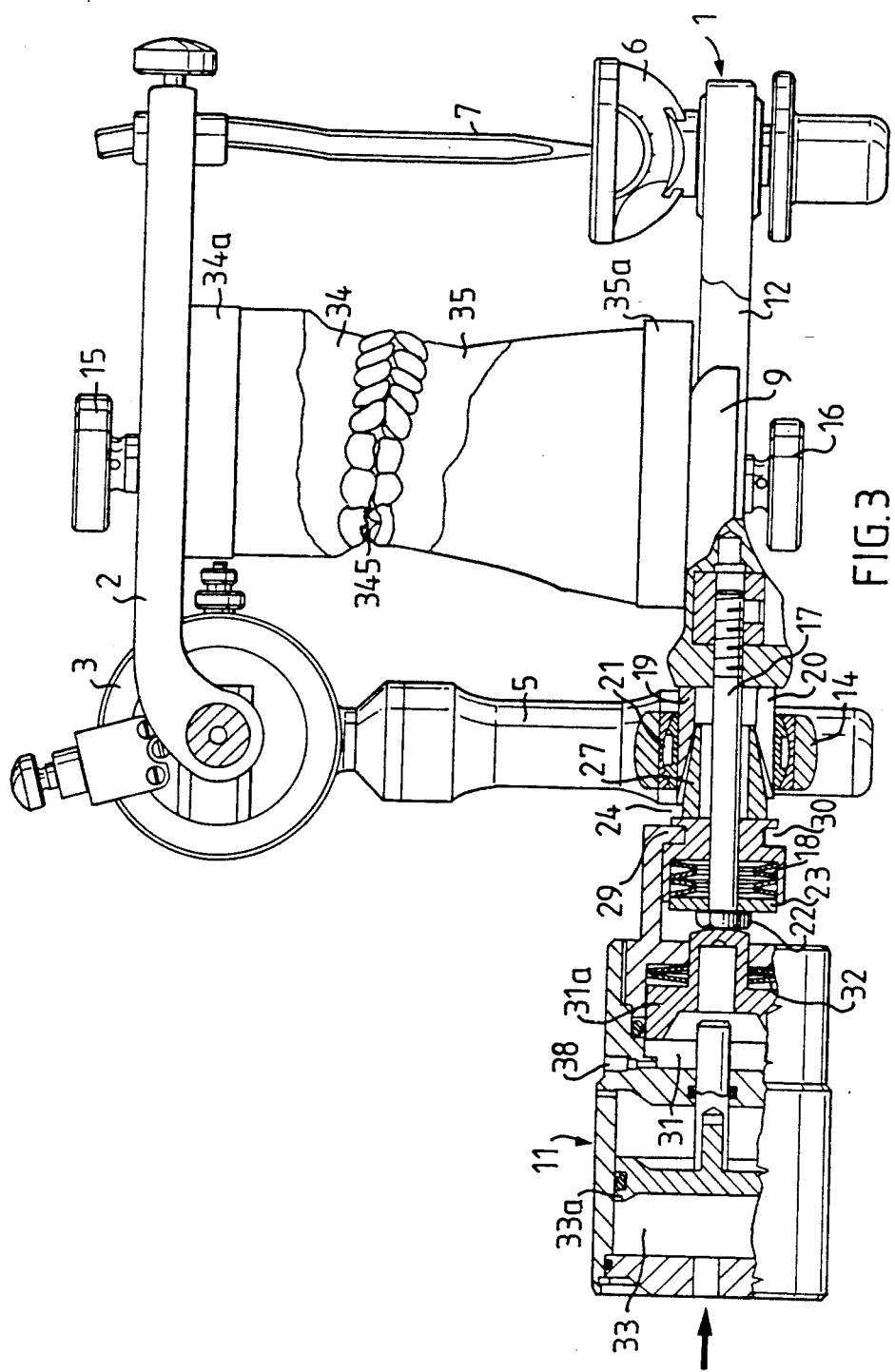
Figure 4A:
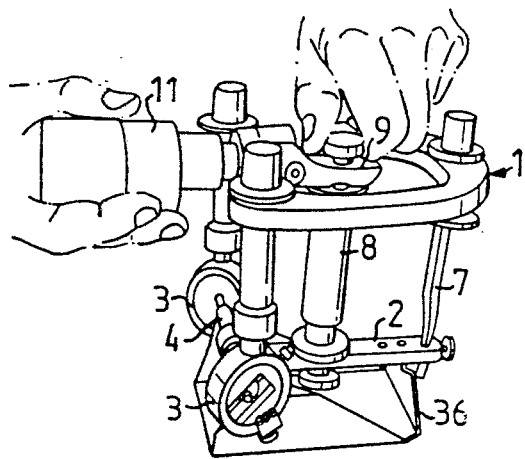
FIG. 4F shows the releasable/lockable arrangement seen from the rear side of the articulator and with the hydraulic/pneumatic device 11 removed and therefore in its locked mode.
FIG. 4G shows how the hydraulic/pneumatic device 11 is adapted to the releasable/lockable arrangement 9.
Figure 4B:
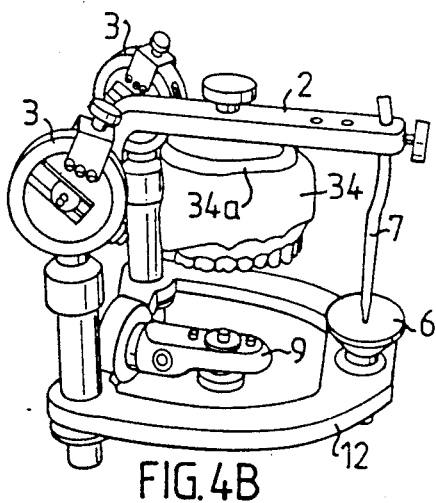
Figure 4C:
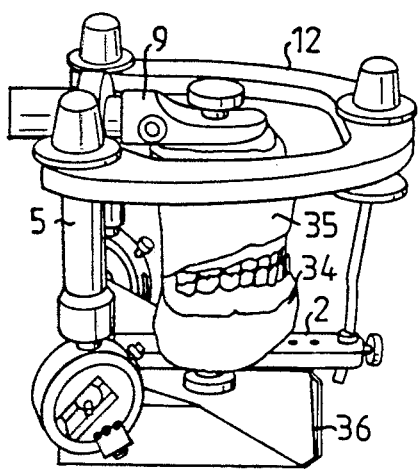
Figure 4D:
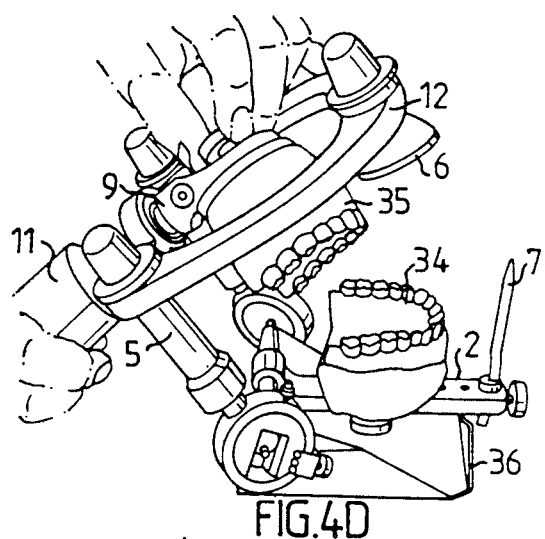
Figure 4E:
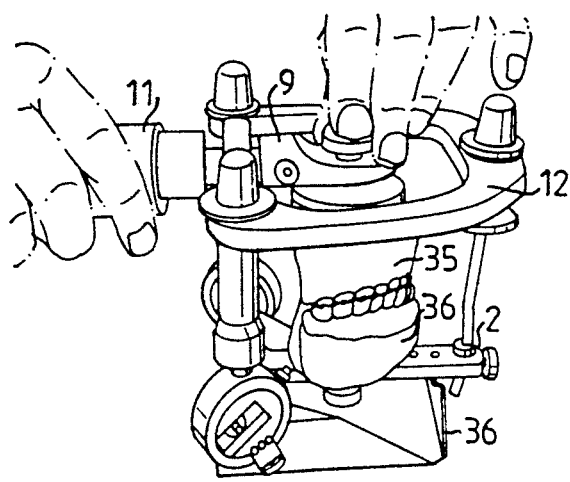
Figure 4F:
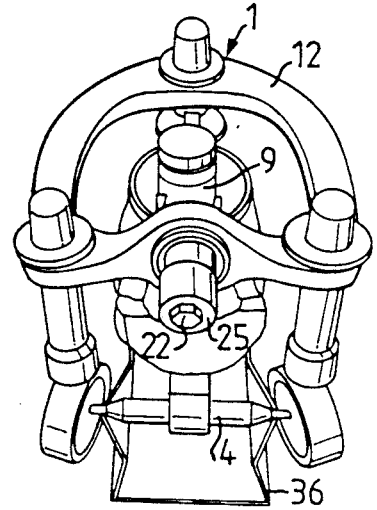
Figure 4G:
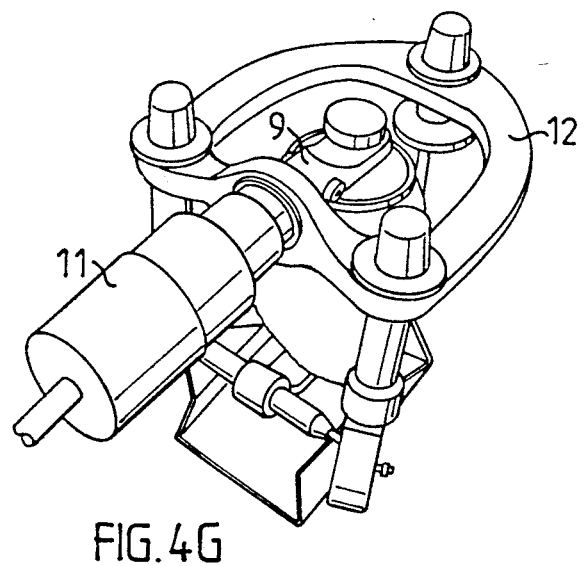
Figure 4H:
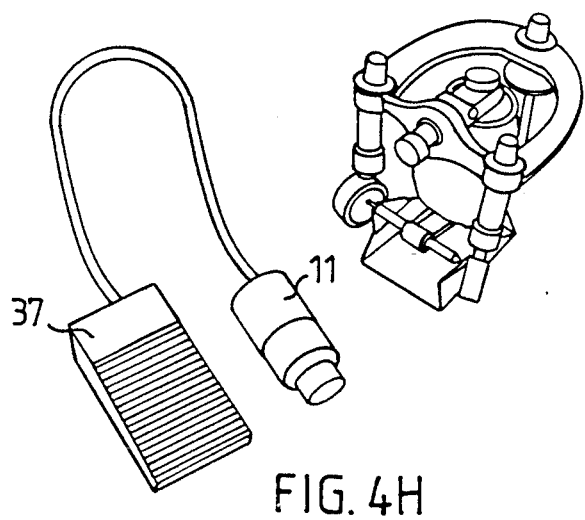

FIG. 4H shows the hydraulic/pneumatic device 11 placed at the side of the articulator. The whole auxillary arrangement for the releasing/locking operations consists of a hydraulic/pneumatic plunger mechanism 11 and a foot pedal control 37. The plunger mechanism being of a hydraulic/pneumatic kind is operated with an air pressure which in this test set was chosen to be an overpressure of 4 bars giving an overpressure of 80 bars in its front hydraulic chamber, and an output power of 600 kp.

The device according to the invention is adapted to a mounting of the casts without plastering and also without any extra equipment such as a hydraulic/pneumatic device to be connected to the articulator during the releasing/locking operation. Yet this embodiment has the quality according to the invention of not requiring any holding power across the casts and the wax index during the locking operation. In this embodiment this feature is achieved by having the locking operation divided into two locking steps.

The second embodiment could be adapted also to an articulator according to the first embodiment or to another kind of articulator requiring a gauge block for its adjustment. In such a case the distance between upper and lower members 41 and 42 of the articulator is adjusted by means of a gauge block like the block 8 shown in FIGS. 1 and 2 and the incisal pin 43 is then adjusted to rest on the incisal table 44. This is not shown but is a starting operation common in the art.

However, in the second embodiment an articulator of ordinary type could be used having a lower member 42 having the support bearing the fastening screw 45 normally intended for fastening the mounting plate for the mandibular cast integral with, i.e. in fixed relation to, the incisal table and the support means 460 of the condylar means 47. According to the invention a movable mandibular cast mounting member 48 is mountable on the lower member 42 by means of the screws 45 instead of the normally fastened mounting plate. An upper maxillary cast mounting member 50 is mountable on the upper member 41 by means of the upper mounting screw 46 instead of the mounting plate.

Figure 7:
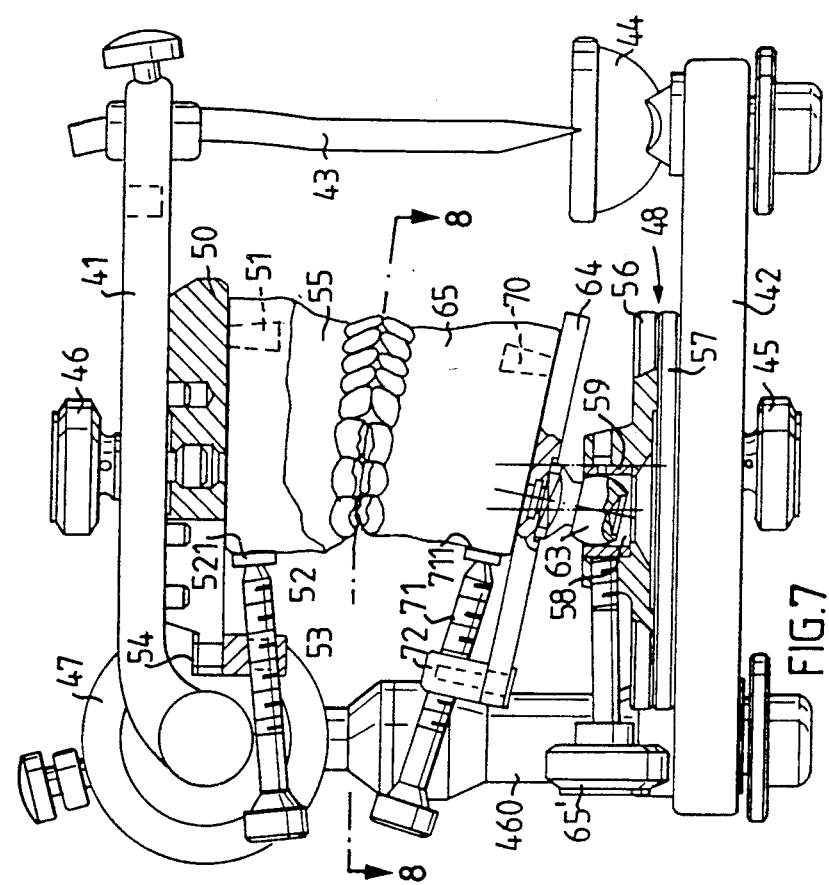

The upper cast mounting member 50 is fixedly mountable on place in the member 41 by the screw 46. It has substantially cylindrical but preferably somewhat conical (having the wider end turned away from the member 50) mounting pins 51 for the maxillary cast 55 which are disposed to abut each tapered side of the front part of the cast (see FIG. 7). A locking screw 52 which in the embodiment shown has its threaded end inclined slightly upwards is mounted at the rear part of the upper member 50 running through a substantially cylindrical threaded holding means 53 fixedly mounted on the member 50 by screwing a threaded pin extending from one of its end surfaces into a threaded hole 54 in the member 50. As seen in FIG. 7 the maxillary cast is locked to the member 50 when it is mounted between the pins 51 and the screw 52 is tightened. However, the inclination of the screw 52 is not critical and it may for instance as well be provided parallel to the surface of the member 50.

Figure 5:
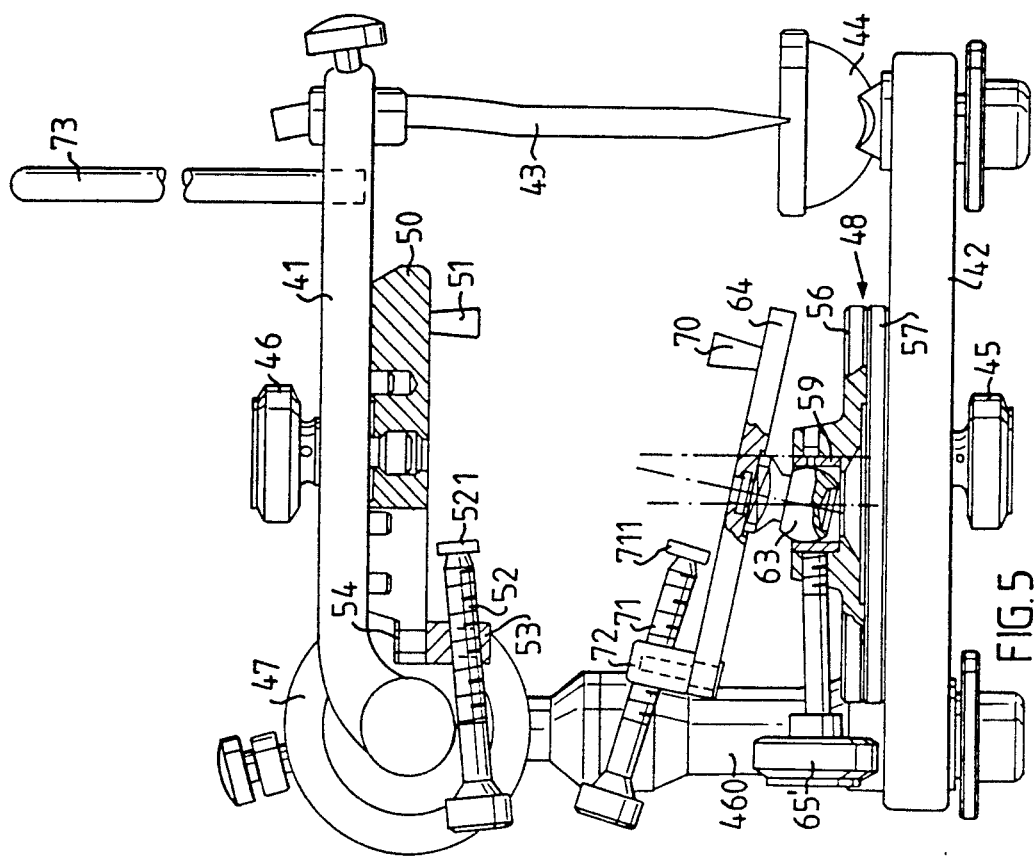
Figure 6:
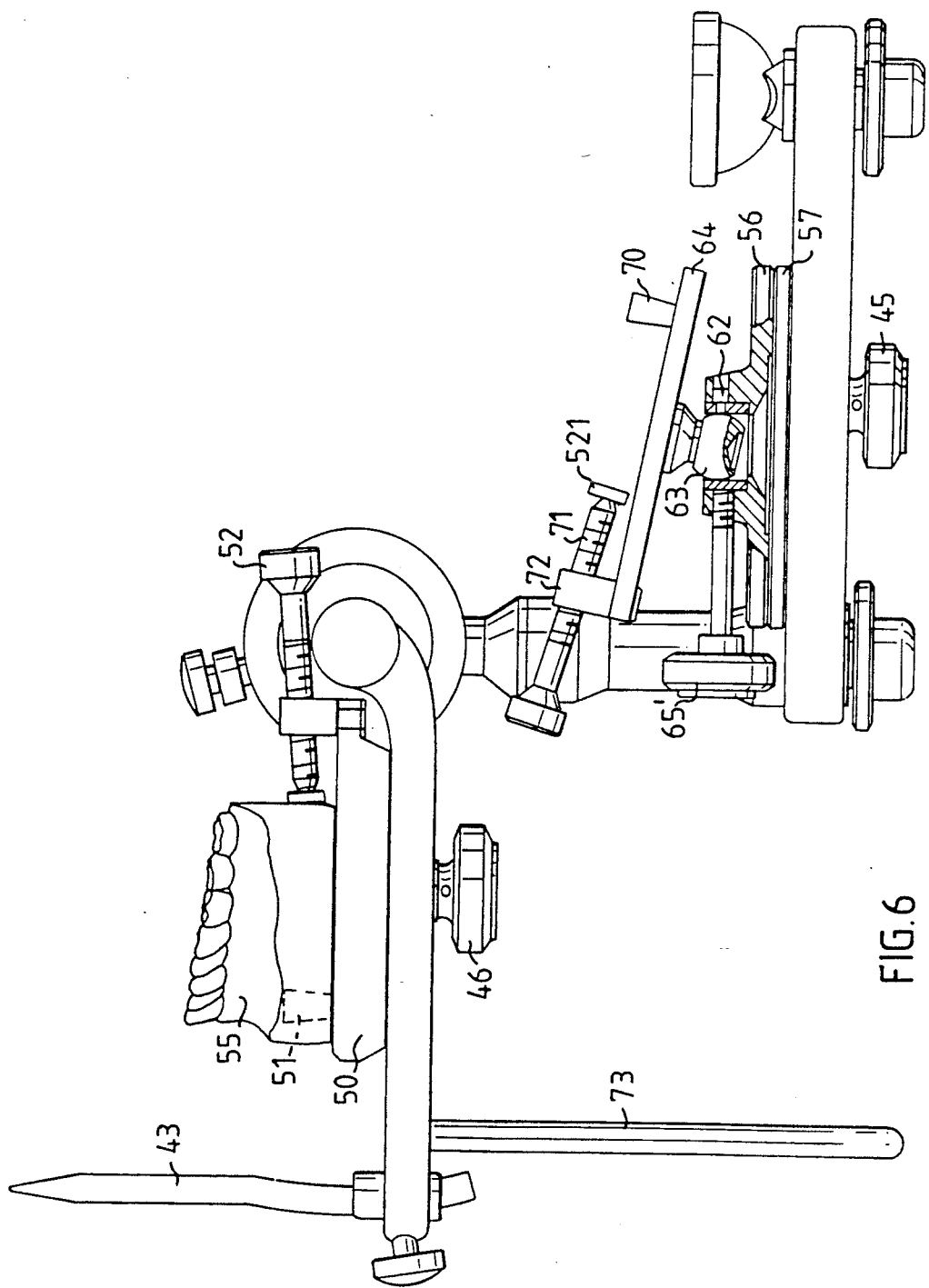

Preferably, the screw 52 has a plate 521 elongated in a plane perpendicular to the plane of the paper in FIGS. 5 to 7 and thus extending along at least a part of the back side of the maxilary cast 55. The plate 521 is pivotally freely movably mounted at the end of the screw 52 such that it adjusts itself to abut the back of the cast along as large a part of its surface as possible. The plate 521 is needed sometimes because the casts have not always straight back sides. Instead they have sometimes a depression in the middle of the back side. However, they have always material at each side onto which the plate 521 has the chance to abut when the screw 52 is tightened.

The lower cast mounting member 48 is divided into two parts 56 and 57 of which the lower part 57 adjacent to the member 42 is fixedly mountable in place with the mounting screw 45. The parts 56 and 57 have preferably a circular periphery and the same diameter. The planar surfaces of the parts 56 and 57 turned to each other are parallel. The upper part 56 has the outer form of a mesa having a cylindrical central opening 58 in which a cylindrical insert 59 is provided which has an axially running slot 60 (see FIG. 9). The slot 60 has a wider part 61 into which a stop screw 62 may enter from the wall of the opening 58 in order to prevent the insertion 59 from falling out from it. The inner diameter of the insert is adapted to hold a spherical means 63 bearing a support means 64 for the mandibular cast 65.

The spherical means 63 is freely movable in the insert 59 both in axial and angular directions but can be locked in a certain position by means of a locking screw 65' provided in the wall of the mess-shaped part 56.

Figure 8:
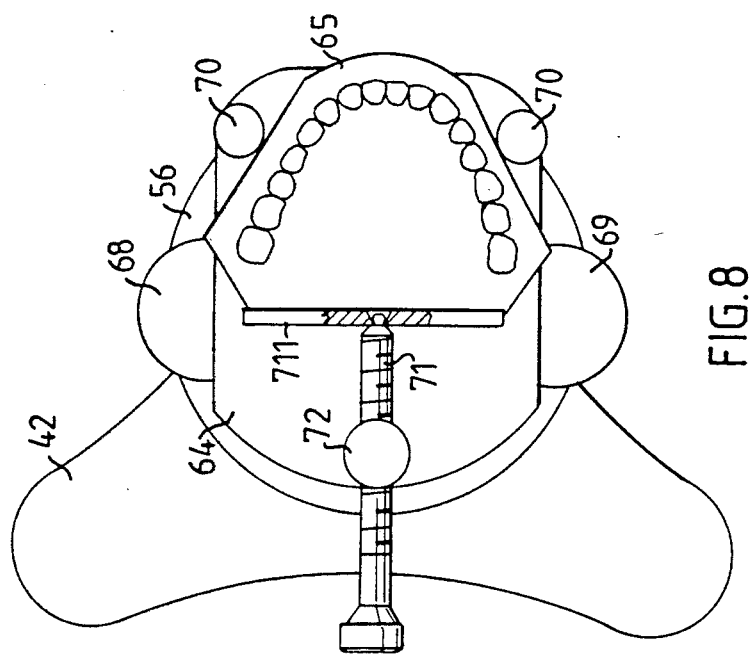
Figure 9:
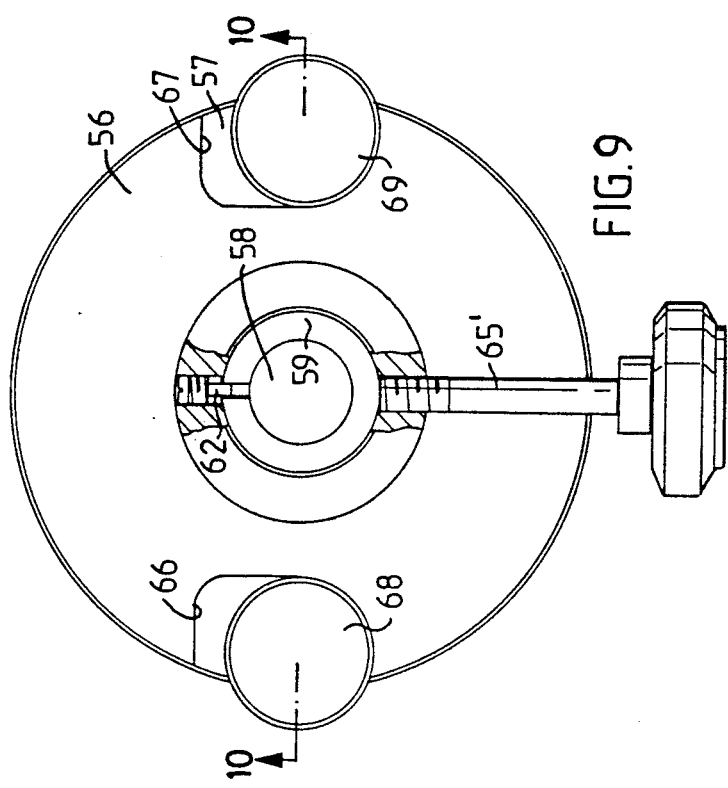
Figure 10:
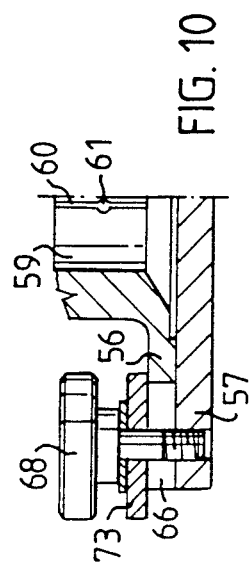

As shown in FIGS. 8 and 9 the upper part 56 has a peripheral part formed like a disk and integral with the central mesa part. This disk has two peripheral cuts 66 and 67 provided approximately diametrically opposite to each other. The size of the cuts has a certain extent. Near the periphery of each cut is a screw 68 and 69, respectively, which is threadingly inserted into the lower part 57. The screws have a collar 73 (see FIG. 10) turned to the part 56, which collar is wide enough to keep the upper part 56 in a fixed relation on the lower part 57 when the screws 68 and 69 are in a tightened condition or mode even when the parts 56 and 57 are displaced in relation to each other. Thus, when the screws 68, 69 are in a released mode the operator can move the upper part 56 along the lower member 42 of the articulator in relation to the lower part 57 within the limits imposed by the cuts 66, 67. Instead of having a collar 73 for each screw 68, 69 a ringshaped plate (not shown) having substantially the same outer diameter as the members 56, 57 and an inner diameter less than the outer diameter of the mesa may be used, the ringshaped plate having a through hole for each screw 68, 69.

Thus the divided releasable/lockable arrangement according to this embodiment is operated by, firstly, the two screws 68, 69 and, secondly, the screw 65'.

The support means 64 is provided with essentially cylindrical pins 70 disposed to abut each tapered front side of the mandibular cast (see FIG. 8) and has a locking screw 71 at its rear part having a threaded holding means 72 of the same kind as the holding means 53 of the screw 52. The screw 71 has preferably a plate 711 having the same construction and function as the plate 521 on the screw 52.

To use the embodiment of the articulator shown in FIGS. 5 to 7, first a pin 73 of some length is screwed into the upper member 41, as seen in FIGS. 5 and 6. When the cast holding devices 50 to 54 and 56 to 72, respectively, are mounted in place as seen in FIG. 5 the operator places the articulator in the opened position shown in FIG. 6 having the upper member supported by the pin 73. The upper maxillary cast 55 is provided on the holding device 50 to 54 and locked place with the locking screw 52. Thereafter, the lower mandibular cast 65 is placed on the holding device 56 to 72 and locked in place with the locking screw 71. Then the articulator is placed in the closed position shown in FIG. 7 and the pin 73 is removed.

If the operator has to repeat the set up procedure of the maxillary cast using a new wax index, the operator loosens the screws 68, 69 and 65', if this has not been done earlier, and turns the articulator upside down placing it on a support of essentially the same kind as the support 36 shown in FIGS. 4A to 4H. The wax index is placed between the casts 55 and 65 and the operator sees to it that the mandibular cast 65 is situated to fit in the wax index by moving the freely movable cast support 64. When the cast 65 has its correct position the operator tightens first the screws 68, 69 and then the screw 65', to fix it in this position.

All casts from human beings have not the same height of the plane in which the teeth of the maxillary and mandibular casts meet. Therefore, some adjustments must sometimes be made which cannot be achieved by a height adjustment of the spherical part 63. Then, an insert (not shown) placed for instance between the member 50 and the cast 55 or between the members 42 and 57 or between the members 57 and 56 or between the member 64 and the cast 650 or between the spherical means 63 and the member 64 may be needed. In the last mentioned case it could be possible to elongate the neck of the part extending from the sphere 63 supporting the plate 64.

We claim:

1. An articulator, for use in making dentures or parts thereof, comprising:
 a) an upper principal member and a lower principal member,
 b) an upper support means for holding a maxillary cast fixedly mounted on the side of said upper member facing said lower principal member,
 c) a lower support means for holding a mandibular cast, said lower support being mounted on said lower principal member and facing said upper principal member,
 d) said lower support having a releasing/locking arrangement to enable moving said lower support freely in several directions when said arrangement is in a released mode and to lock it in a desired position requiring only a slight holding in place of the casts in relation to each other by an operator during a locking procedure, said releasing/locking arrangement having a bushing arrangement on a stationary part of said lower principal member which allows said support means to move in both angular and axial directions in relation to said stationary part only when the releasing/locking arrangement is in said released mode and also having a spring loaded locking arrangement normally locking said lower support means in said bushing arrangement in a fixed relation by spring force, and wherein a device adapted to be powered by an external power source releases said spring force when powered and imposes said spring force when unpowered.

2. An articulator according to claim 1, wherein said powerable device is separable from the articulator when unpowered.

3. An articulator according to claim 1, wherein said external power source is a source of fluid pressure.

4. An articulator for use in making dentures or parts thereof, comprising an upper principal member and a lower principal member, an upper support means for holding a maxillary cast fixedly mounted on the side of said upper member facing said lower principal member, a lower support means for holding a mandibular cast, said lower support being mounted on said lower principal member and facing said upper principal member, wherein said articulator is provided with an accessory including:
 detachable mandibular cast mounting means (48) adapted to be mounted detachably on said lower support,
 said detachable means including:
  i) a first part (57), which is fixedly but detachably mounted in place on said lower support,
  ii) means (64) on said first part (57) for holding said mandibular cast,
  iii) a second part (56) holding said mandibular cast holding means (64) and mounted on said first part (57) and having a releasing/locking arrangement (68, 69, 58, 59, 63, 65) such that said mandibular cast holding means is freely movable in several directions when said arrangement is in a released mode and lockable in a desired position requiring only a slight holding in place of the cast in relation to each other by an operator during a locking procedure, said releasing/locking arrangement including a first releasing/locking means (68, 69) attaching said second part (56) to said first part (57) thereby making said second part (56) slidable in relation to said first part (57) when said arrangement is in its released mode, and a second releasing/locking means (58, 59, 63, 65) holding said holding means (64) movable both angularly and in vertical direction when said second means is in its released mode.

5. An articulator according to claim 4, wherein said mandibular cast holding means includes an arrangement (70, 71, 72) for holding said mandibular cast (65) without plastering.

6. An articulator according to claim 5, wherein said holding arrangement comprises pins (70) adapted to abut tapered front sides of said mandibular cast (65) and a locking screw means (71, 72) on a rear side of said cast (65) pressing against the rear side of said cast (65) when tightened.

7. An articulator for use in making dentures or parts thereof, comprising an upper principal member and a lower principal member, an upper support means for holding a maxillary cast fixedly mounted on the side of said upper member facing said lower principal member, a lower support means for holding a mandibular cast, said lower support being mounted on said lower principal member and facing said upper principal member, wherein said articulator is provided with an accessory including:

detachable mandibular cast mounting means (48) adapted to be mounted detachably on said lower support, said detachable means including:

i) a first part (57), which is fixedly but detachably mounted in place on said lower support, ii) means (64) on said first part (57) for holding said mandibular cast, iii) a second part (56) holding said mandibular cast holding means (64) and mounted on said first part (57) and having a releasing/locking arrangement (68, 69, 58, 59, 63, 65) such that said mandibular cast holding means is freely movable in several directions when said arrangement is in a released mode and lockable in a desired position requiring only a slight holding in place of the casts in relation to each other by an operator during a locking procedure, said releasing/locking arrangement including a first releasing/locking means (68, 69) attaching said second part (56) to said first part (57) thereby making said second part slidable in relation to said first part (57) when said arrangement is in its released mode, said first releasing/locking means (68, 69) comprising locking screws threadingly inserted into said first part (57) and said second part (56) having cuts (66, 67) through which said locking screws are inserted.

8. An articulator according to claim 7, wherein said second releasing/locking means (58, 59, 63, 65) includes a cylindrical opening (58), in which a spherical means (63) bearing a support means (64) for said mandibular cast (65) is disposed, and a locking screw (65') in the wall of said cylindrical opening (58) for locking said spherical means (63) against movement.

* * * * *